US005650319A

United States Patent [19]
Masuho et al.

[11] Patent Number: 5,650,319
[45] Date of Patent: Jul. 22, 1997

[54] HUMAN MONOCLONAL ANTIBODY TO GLYCOPROTEIN GPIII OF VARICELLA ZOSTER VIRUS

[75] Inventors: Yasuhiko Masuho, Hino; Toru Sugano, Machida; Takami Tomiyama, Hino; Satoshi Sasaki, Hachioji; Tsuyoshi Kimura; Takashi Kawamura, both of Hino; Yohichi Matsumoto, Musashino, all of Japan

[73] Assignee: Teijin Limited, Osaka, Japan

[21] Appl. No.: 89,616

[22] Filed: Jul. 12, 1993

Related U.S. Application Data

[63] Continuation of Ser. No. 781,267, filed as PCT/JP91/00519, Apr. 19, 1991, published as WO91/16448, Oct. 31, 1991, abandoned.

[30] Foreign Application Priority Data

Apr. 20, 1990 [JP] Japan .................... 2-103132

[51] Int. Cl.⁶ ................. C12N 5/28; C07K 16/08
[52] U.S. Cl. .................... 435/240.27; 530/388.3
[58] Field of Search .............. 435/172.2, 240.1, 435/240.27; 530/388.1, 388.15, 388.3, 388.85

[56] References Cited

U.S. PATENT DOCUMENTS 4,950,595  8/1990  Masuho et al. ............... 530/388.15

FOREIGN PATENT DOCUMENTS 0211756  2/1987  European Pat. Off. .
62-42933  of 0000  Japan .

OTHER PUBLICATIONS

P.M. Keller et al. J. Virol. 52(1):293–297 Oct. 1984.

T. Sugano et al. J. Gen. Virol. 72:2065–2073 1991.

WE Friedrichs et al. J. Virol. 49(3):992–996 Mar. 1984.

B. Forghani et al. J. Virol. 52(1):55–62 Oct. 1984.

E. Montalvo et al. Virology 149:230–241, 1986.

Dubey et al. (1988) J. Infect. Diseases 157(5), 882–888.

Larussa et al. (1987) J. Clinic. Microbiol. 25(11), 2059–2062.

*Primary Examiner*—Mindy Fleisher
*Assistant Examiner*—Terry A. McKelvey
*Attorney, Agent, or Firm*—Sughrue, Mion, Zinn, Macpeak & Seas

[57] ABSTRACT

The human monoclonal antibody to the glycoprotein gpIII of varicella zoster virus (VZV), and hybridoma producing same, are provided. The hybridoma is obtained by immunizing human lymphocytes with gpIII antigen in the presence of a mitogen, and selecting a monoclonal antibody which reacts with a cell monolayer ELISA plate but substantially does not react with a cell homogenate ELISA plate.

4 Claims, 8 Drawing Sheets

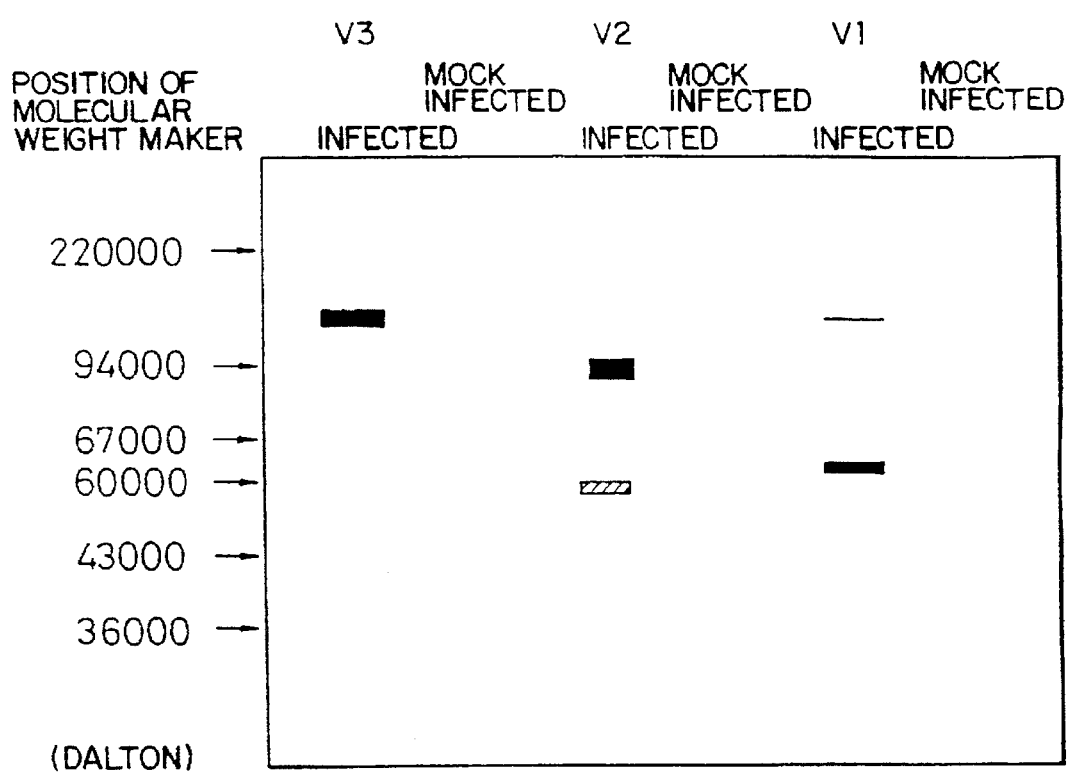

HUMAN MONOCLONAL ANTIBODY TO GLYCOPROTEIN GPIII OF VARICELLA ZOSTER VIRUS

This is a continuation of application Ser. No. 07/781,267 filed Dec. 18, 1991, now abandoned, which is a 371 of PCT/JP91/00519, filed Apr. 19, 1991, published as WO91/16448, Oct. 31, 1991.

TECHNICAL FIELD

The present invention relates to human monoclonal antibodies (HuMAb) to the gpIII protein of the varicella zoster virus (VZV), and cell lines producing same.

An object thereof is to provide HuMAb specific to VZV, useful for a diagnosis and prophylaxis, as well as treatment, of viral infections and diseases caused by VZV.

BACKGROUND ART

VZV is a virus which causes varicella, encephalitis, hepatitis or the like by primary infection, and after entering a latent stage, sometimes relapses as varicella zoster.

It is known that varicella in immunocompromised hosts sometimes becomes fatal to the host, and zoster sometimes causes post herpetic neuralgia after recovery from the disease.

As drugs for these diseases Acyclovir (Wellcome, England), varicella live vaccine (Research Institute for Microbial Diseases Osaka University, Japan), BV-Ara U (Yamasa Shoyu, Japan) and the like are mentioned, but these do not have satisfactory safety and effectiveness, and therefore, the development of drugs which can be prophylactically administered and have high safety and effectiveness, is required.

It was recognized that a human immunoglobulin formulation obtained from human serum after suffering from varicella zoster (Varicella-Zoster Immune Globulin: VZIG; trade name Varitect, etc.) is effective to some extent (Zaia, J. A. et al., J. Infect. Dis. Vol. 147, pp 737–743, 1983), but the neutralization titer of VZIG against VZV is only several or several tens of times that of a conventional human immunoglobulin formulation, and therefore, drugs having a higher neutralization titer are needed. Moreover, a supply of VZIG is difficult, and there are problems of cost and maintaining a constant supply. In addition, human serum is intrinsically accompanied by the risk of contamination with unknown factors such as the AIDS virus or the like. To solve these problems, MAbs to VZV have been developed.

Some groups (Friedrichs, W. E., and Grose, C., J. Virol. Vol. 49, pp 992–996, 1984; Keller, P. M. et al., J. Virol. Vol. 52, pp 293–297, 1984; Forghani, B. et al., J. Virol. Vol. 52, pp 55–62, 1984) prepared mouse monoclonal antibodies (mouse MAb) which specifically bind to VZV or a glycoprotein of 105–118 k Daltons present in a cell infected with VZV and designated as gpIII or gA (hereinafter abbreviated as gpIII; see, Davison, A. J. et al., J. Virol. Vol. 57, pp 1195–1197, 1986).

Where, however, a mouse monoclonal antibody is administered to a human, it is recognized as a heterologous protein, and may cause side effects such as anaphylatic shock. Moreover, the mouse MAb is known to be depleted from the blood rapidly by human antibodies produced in vivo against the mouse MAb. This offsets the advantages of a protein having a low toxicity and high stability.

Therefore, for treatment of VZV infectious diseases, a human-type MAb (HuMAb) is required.

As the HuMAb to VZV, there are known HuMAb (Foung, S. K. et al., J. Infect. Dis. Vol. 152, pp 280–285, 1985) to a glycoprotein of VZV designated as gpII or gB (hereinafter abbreviated as gpII; see, Davison, A. J. et al., J. Virol. Vol. 57, pp 1195–1197, 1986), and HuMAb (see, Sugano, T. et al., Eur. J. Immunol., Vol. 17, pp 359–364 and Japanese Unexamined Patent Publication No. 62-42933, and EP No. 0198086 and U.S. Pat. No. 4,950,594) to a glycoprotein of VZV designated as gpI or gC (hereinafter abbreviated as gpI; see, Davison, A. J. et al., J. Virol., Vol. 57, pp 1195–1197, 1986).

The neutralizing activity of HuMAb to gpI, however, is dependent on complement, and therefore, the neutralizing activity is remarkably reduced when complement is not added. Moreover, although HuMAb to gpII does not need the addition of complement for neutralizing activity, its neutralization titer (in terms of the amount of antibody which neutralizes 50% of the virus) is lower than that of HuMAb to gpI in the presence of complement.

Studies have been made using mouse MAb, to determine which antigen of VZV is most suitable for prevention of an infection by VZV. According to Keller et al. (Keller, P. M. et al., J. Virol., Vol. 52, pp 293–297, 1984), although antibody to gpIII exhibited a high neutralizing activity regardless of the presence or absence of complement, antibody to the gpI neutralized virus only with the addition of complement and many of the antibodies to gpII did not neutralize the virus, regardless of the presence or absence of complement. Similar results were revealed by Grose, C. H. et al. (Grose, C. H. et al., Inf. Immun., Vol. 40, pp 381–388, 1983) and Forghani B. et al. (Forghani B. et al., J. Virol., Vol. 52, pp 55–62, 1984). Moreover, it is known that an MAb to gpIII of VZV inhibits the spread of VZV from an infected cell to a noninfected cell (intercellular infection-inhibiting activity or virus spread-inhibiting activity). This activity was not found for MAb's to the gpI or gpII.

It has been revealed that antibody to gpIII is important for prophylaxis and treatment of varicella. According to Dubey L. et al. (Dubey L. et al., J. Infect. Dis., Vol. 157, pp 882–888, 1988), among leukemia patients to whom a varicella vaccine was administered, those patients suffering from varicella had antibodies to gpI and gpII, but did not have antibodies to gpIII. Among these patients, those patients who recovered were shown to have an increased antibody titer to gpIII.

As seen from the above, it has been attempted to develop HuMAb to gpIII of VZV, which has a high virus-neutralizing activity and a virus spread-inhibiting activity, for prophylaxis and treatment of VZV infectious diseases, but HuMAb to gpIII of VZV has not been obtained.

It is considered that one reason why it is difficult to obtain HuMAb to gpIII in comparison to obtaining HuMAb to gpII is because the amount of antibodies to gpIII produced in a human body is low due to low immunogenicity of gpIII. It is known that when a guinea pig is immunized with an antigen, the production of antibodies to gpIII is low (Keller, P. M. et al., J. Virol. Methods, Vol. 14 pp 177–188, 1986), and that the production of antibodies to gpIII in the human body is also low (Brunell, P. A. et al., J. Infect. Dis., Vol. 156, pp 430–435, 1987).

The above-mentioned low production of antibody in the human body means that the number of lymphocytes which produce antibodies to gpIII is small, and therefore the probability of obtaining a hybridoma which produces HuMAb to the gpIII prepared using those human lymphocytes, is low. This is clear from the experimental results of the present inventors shown in FIG. 2.

Moreover, another reason for the heretofore difficulty in obtaining HuMAb to gpIII is that it is very difficult to detect an antibody to gpIII by ELISA or the like, using disrupted VZV-infected cells as an antigen, as is currently used (Grose et al., J. Infect. Dis. Vol. 157, pp 877–881, 1988). This is also clear from the experimental results of the present inventors shown in FIG. 3B.

Generally, in comparison to gpI and gpII, only a very small amount of gpIII is present in an antigen obtained by disrupting VZV-infected cells, therefore in a screening system using such an antigen, the probability of selecting an antibody to gpIII was very low, and most MAbs selected by such a screening system were antibodies recognizing gpI or gpII (Sugano et al., Eur. J. Immunol., 17, 359–364, 1987).

DISCLOSURE OF THE INVENTION

The present inventors created the present invention by solving the above-mentioned various problems, through the use of the methods described hereinafter in detail.

Accordingly, the present invention provides HuMAb to the gpIII glycoprotein of VZV.

The present invention also provides a hybridoma producing said HuMAb.

BRIEF DESCRIPTION OF THE DRAWINGS

FIGS. 4A and 4B show 96-well plates used for screening by V-SIMA (Virus Spread Inhibition Micro Assay). FIG. 4B schematically shows FIG. 4A, wherein blank circles are wells exhibiting a virus spread-inhibiting activity.

FIG. 5 represents an identification of antigens by immunoprecipitation. Anti-gpIII HuMAb (V3) immunoprecipitated a 118,000 dalton gpIII antigen of VZV-infected cells.

EMBODIMENTS OF CARRYING OUT THE INVENTION

Figure 1:
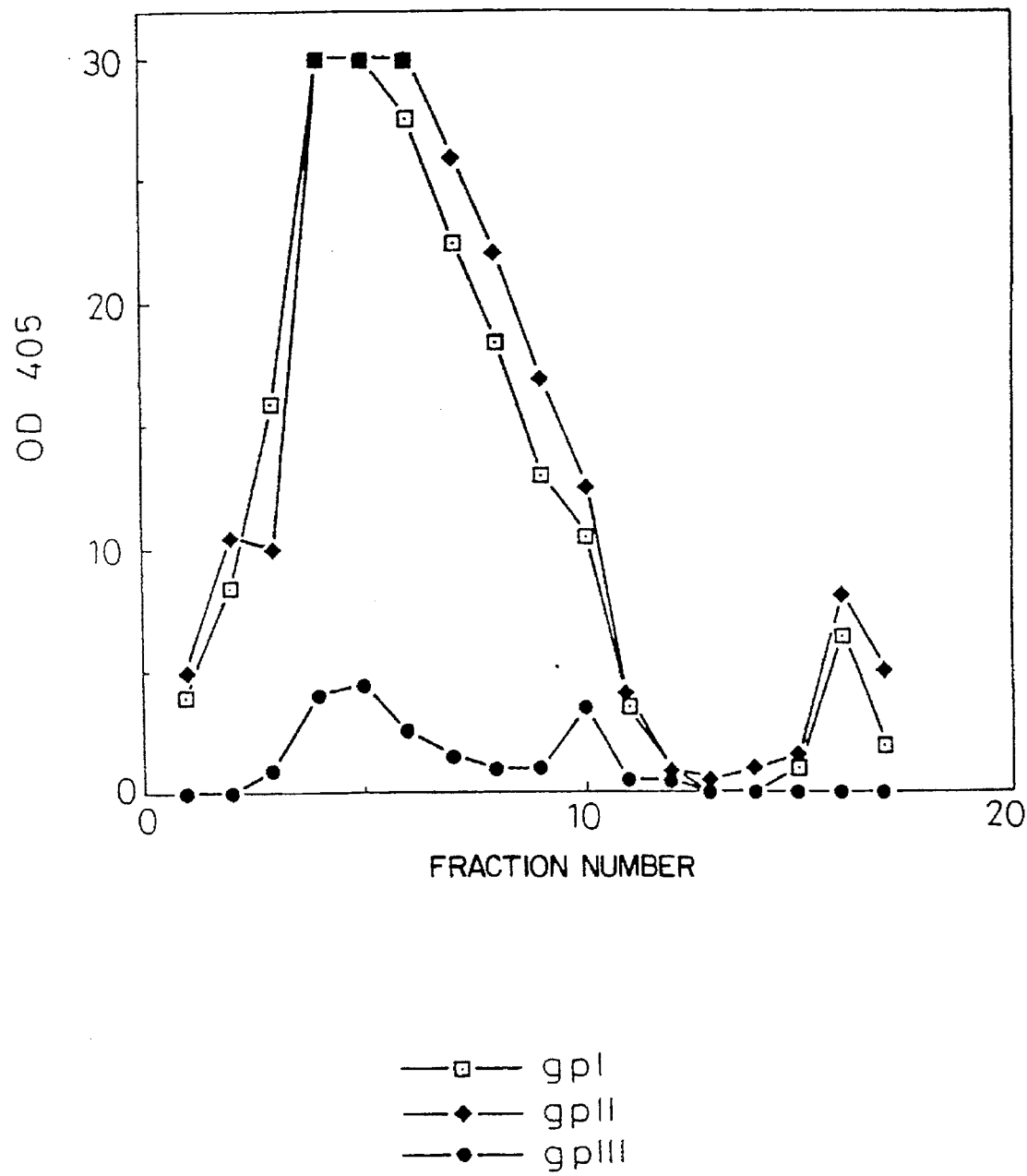
FIG. 1 shows the fraction of antigens used for in vitro immunization. Fractions obtained by subjecting VZV to a sucrose density gradient centrifugation were immobilized on a plastic plate, and mouse anti-gpIII monoclonal antibody was reacted therewith. Fraction No. 10 is a fraction containing much gpIII antigen, and therefore, this was used as an antigen for in vitro immunization.

The present inventors recognized that difficulties in the construction of HuMAb to the gpIII glycoprotein of VZV lie in the following three points, overcame these problems by intense investigations, and established a hybridoma continuously producing HuMAb to the gpIII glycoprotein of VZV.

a) The number of cells (B lymphocytes) producing antibodies to gpIII of VZV in the human body is small.

b) A specific and simple method of detecting HuMAb which binds to gpIII of VZV is necessary.

c) A simple method of assaying anti-viral activity of HuMAb to gpIII of VZV is necessary.

As a means for solving the above-mentioned problem (a), since it is impossible to immunize a human with VZV or gpIII glycoprotein of VZV as an antigen, human lymphocytes taken out of the body were stimulated in vitro with an antigen and mitogen to proliferate cells producing an antibody to gpIII of VZV.

Human lymphocytes are isolated from human peripheral blood, tonsils, adenoids, bone marrow, spleen or the like, but preferably cells isolated from the spleen are used.

As an antigen, VZV, VZV-infected cells, gpIII glycoprotein of VZV, or the like is used, and preferably purified VZV or gpIII glycoprotein is used.

As a mitogen for stimulating differentiation and proliferation of lymphocytes, pokeweed mitogen (PWM), phytohemagglutinin (PHA), concanavalin A, protein A or the like may be used, but preferably PWM is used. In place of a mitogen, a B-cell growth factor (BCGF), B-cell differentiation factor (BCDF), interleukin 2 (IL-2), interleukin 4 (IL-4), interleukin 6 (IL-6) or the like also can be used as a differentiation/growth factor for lymphocytes.

The concentration of antigen is 1 ng/ml to 10 µg/ml, preferably 1 to 10 ng/ml; the concentration of lymphocytes is suitably $1 \times 10^5$ to $1 \times 10^7$/ml; the culture temperature is 35° to 40° C.; and the culture period is 4 to 14 days, preferably 6 to 8 days. The culture medium is preferably a medium containing 5 to 20% fetal calf serum, such as RPMI 1640 or GIT (Nippon Seiyaku K.K., Tokyo Japan).

In vitro-stimulated human lymphocytes thus obtained are transformed into immortal cell lines, by a known method. For example, they are converted into hybrid cells by cell fusion with mouse myeloma cells or human myeloma cells, or with hetero myeloma cells (Japanese Unexamined Patent Publication No. 61-124380) or transformed to cell lines having endless growth ability, by infection with Epstein Barr virus (EBV).

Where transformed with EBV, to obtain a cell line which continues to stably produced HuMAb, the EBV-transformed cells are preferably fused with mouse myeloma cells.

The cell lines thus obtained, which produce HuMAb to gpIII of VZV, are screened by methods described hereinafter (means for solving the problems b) and c)), cloned, and established as a cell line stably producing HuMAb to the gpIII of VZV.

To solve the above-mentioned problem b), the present inventors established the following novel screening system. The present inventors found that a mouse MAb which binds to gpIII of VZV strongly binds to an ELISA plate to which intact VZV-infected cells have been immobilized with formaldehyde or glutaraldehyde (monolayer plate), while it binds only slightly to an ELISA plate to which a sonicated VZV-infected cell suspension has been immobilized (homogenate plate). On the other hand, MAb which reacts with both gpI and gpII of VZV strongly reacted with both the ELISA plates. Accordingly, to select a HuMAb which specifically binds to gpIII of VZV, HuMAb, which strongly reacts with a monolayer plate but does not react with a homogenate plate, was selected.

These ELISAs are described in detail in the Examples.

As a means of solving the above-mentioned item c), the present inventors noted that MAb to gpIII of VZV, in contrast to anti-gpI MAb and anti-gpII MAb, inhibits cell to cell infection of virus as shown by Keller P. M. et al. (Keller P. M. et al., Virology Vol. 157, pp 526–533, 1987), and thus increased the sensitivity so that this activity can be detected for a trace amount of antibody contained in a hybridoma supernatant, and developed a method that can rapidly, simply and quantitatively measure a trace amount of an antibody (V-SIMA, Virus-Spread Inhibition Micro Assay). This method is now described.

VZV-sensitive cells, such as primary monkey kidney cells, human myeloma cells or human fetal fibroblast cells were distributed in a 96-well culture plate at a concentration of $1 \times 10^4$ to $1 \times 10^6$ cells/ml, and cultured at 35° to 40° C. for one to five days to form a cell monolayer. Any VZV-infective cells can be used, but preferably human embryonic lung fibroblast cells (HEL), MRC-5 or WI-38 are used. Also, any culture medium in which the above-mentioned cells are grown can be used, but preferably Eagle's Minimum Essential Medium (Eagle's MEM) or DMEM (Dulbecco's Minimum Essential Medium) is used.

Next, the culture medium is sucked off, and VZV-infected cells suspended in the culture medium are distributed at a concentration of $2 \times 10^2$ to $2 \times 10^5$ cells/ml. The cells are prepared by co-culturing VZV-infected cells with VZV-noninfected cells at a ratio of 1:5 to 1:20, and cultured for 1 to 3 days. Preferably, the cells are suspended at a concentration of $1 \times 10^5$ to $1 \times 10^7$ cells/ml in a freezing medium containing 4 to 40% fetal bovine serum or calf serum and 5 to 10% dimethylsulfoxide, distributed and lyophilized. The smaller the number of VZV-infected cells, the higher the V-SIMA sensitivity, and thus preferably the cells are inoculated in an amount of 25 to 100 μl per well at a concentration of $4 \times 10^3$ to $2 \times 10^4$ cells/ml.

Next, 100 to 200 μl/well of a hybridoma culture broth containing an antibody is added, and incubation is carried out for 1 to 3 days at 35° to 40° C. Preferably, the incubation is continued until a cytotopathic effect appears in 30 to 80% of cells in a well to which VZV-infected cells alone have been inoculated. Next, each well is washed several times with 0.01M phosphate buffer (pH 6.5 to 7.5) (PBS) containing 0.15M sodium chloride, and fixation is carried out with PBS containing 0.05 to 0.2% glutaraldehyde or 0.1 to 10% formaldehyde.

After further washing with PBS, PBS containing 1 to 5% bovine serum albumin (blocking solution) is added at 37° C. for more than 1 hour to block the reaction. If necessary, the plate including the blocking solution in wells, can be stored at 4° C. for one month. After each well is washed with PBS containing 1% bovine serum albumin (washing solution), infected cells are stained by an enzyme immunoassay according to the following process. For example, as the first antibody, any antibody reactive with a VZV antigen specifically can be used, but preferably MAb, rabbit polyclonal antibodies or the like to the gpI or gpII are used. After reacting the first antibody at room temperature, unreacted first antibody is removed by washing, and an enzyme-labeled second antibody reactive with the first antibody is added for reaction. As an enzyme, peroxidase, alkaline phosphatase, β-galactosidase or the like is used, but preferably horseradish peroxidase is used. The second antibody is reacted at room temperature and removed by washing, and a substrate solution to be colored by the enzyme reaction is added.

For example, where a peroxidase is used as an enzyme, $H_2O_2$ is used as a substrate, and TMBZ-HCl (tetramethyl benzyzine HCl) or 4-chloro-1-naphthol is used as a coloring agent.

The substrate solution is colored by TMBZ-HCl and the absorbance at a wavelength of 650 nm is quantitated. The reaction can be also terminated by the addition of 1N sulfuric acid, and the absorbance at a wavelength of 450 nm can be measured. Where 4-chloro-1-naphthol is added, the colored pigment becomes insoluble and is deposited on fixed VZV-infected cells, and thus a visible determination is possible. Coloration by an enzyme immunoassay is not limited to a particular method, and any method which specifically stains VZV-infected cells or causes coloring of a substrate reflecting the number of VZV-infected cells can be used. For example, a first antibody directly labeled with an enzyme, or a biotinated first antibody and an avidin-linked enzyme, can be used.

The substrate should be selected according to the particular enzyme, and the kind and concentration thereof is not limited.

Thus, by staining or coloring a substrate, the amount of VZV-infected cells can be determined, and the extent to which an antibody inhibits infection of VZV from cell to cell, can be determined.

As described above, it is possible to proliferate human lymphocytes producing an antibody to gpIII of VZV by stimulating in vitro, to immortalize the cells by cell fusion or EBV-transformation, to select a cell line producing HuMAb, preferably human IgG, specifically binding to the gpIII of VZV, by using a cell monolayer plate and cell homogenate plate, and to select and establish a cell line producing HuMAb having a high activity to prevent cell to cell infection of VZV, by a V-SIMA method.

The established cell line is stably grown in a medium suitable for cell growth, for example, a fetal bovine serum- or calf serum-supplemented RPMI 1640, DMEM, HAM, GIT or the like, or a serum-free medium, to secrete HuMAb to the medium.

The present cell line can be frozen, and can be cultured in a large amount by a suitable method. Such a cell line is, or replicated cells are, included in the scope of the present invention. Moreover, cell lines producing HuMAb to the gpIII of VZV substantially the same as that of the above-mentioned cell line and HuMAb produced are included in the scope of the present invention, regardless of the construction process thereof.

Although HuMAb to gpIII of VZV is believed to be useful for the prophylaxis and treatment of VZV-infection diseases, and the like, this has not yet been established.

The reason for the difficultly in establishing a cell line producing HuMAb to gpIII of VZV is that the number of cells producing an antibody specific to gpIII of VZV is small among human lymphocytes, and an effective method of screening the antibody has not been established.

According to the present invention, a process for proliferating lymphocytes producing a gpIII specific antibody by in vitro stimulation of lymphocytes, and for effectively screening the antibody, has been accomplished, and cell lines producing a derived HuMAb to gpIII of VZV have been established. The established cell lines can be grown while stably producing HuMAb, and a large amount of anti-gpIII human monoclonal antibodies can be produced.

Cell lines of the present invention can be cultured in a large amount to produce a large amount of HuMAb to gpIII of VZV in a culture supernatant. The HuMAb is concentrated and purified by anion exchange chromatography, cation exchange chromatography, affinity chromatography, gel filtration chromatography and the like, and holds promise as pharmaceuticals effective for the prophylaxis or treatment of VZV infectious diseases. Advantages of the present HuMAb used as pharmaceuticals for prophylaxis or treatment of VZV infection diseases are high safety, a long half time in the blood, and a high anti-viral titer.

EXAMPLES a) Preparation of a VZV antigen for in vitro stimulation

To HEL cells (human embryonic lung fibroblast cells) cultured in monolayer in a culture flask having a bottom area of 150 cm$^2$ (CORNING N.Y. 14831 USA) was added ⅕ volume of VZV-infected HEL cells, and incubation was carried out at 37° C. in 5% $CO_2$ (hereinafter, the culture conditions are 37° C. and 5% $CO_2$, unless otherwise defined). When the cytopathic effect appeared in about 80% of the cells, monolayer cells were once washed with PBS, and detached with PBS containing 1 mM EDTA to recover the cells. The cells were washed twice with Hank's balanced salt solution (HBSS), suspended in 1 ml of SPGA solution/ $1\times10^7$ cells (10 mM potassium phosphate buffer, pH 7.4, containing 0.218M sucrose, 0.0049M sodium glutamate and 1% BSA), and sonicated for one minute using a sonicator (MS-50 HEAT SYSTEMS, Ultrasonics INC. N.Y. USA) at 50 W, 23 kHz, to disrupt the cells. Cell debris was removed by centrifugation at 3000 rpm for 15 minutes, and intracellular particles were removed by centrifugation at 12500 rpm (Hitachi RPR20-2). Then 8 ml of the supernatant was overlaid on a 20%–80% sucrose density gradient (25 ml) in 20 mM Tris-HCl buffer (pH 7.4) containing 1 mM EDTA, and centrifuged at 27000 rpm (Hitachi SRP28A), at 4° C., for one hour.

Of the 2 ml fractions obtained, 10 μl of each fraction was diluted with 40 μl of 0.05M carbonate buffer solution (pH 9.5)/the diluted solution was put into wells of a 96-well plate (Falcon 3912, Becton Dickinson and Co. OXNARD Calif. 93030 USA) for reaction, and the protein in each well was fixed. After blocking the wells with PBS containing 1% bovine serum albumin (BSA), 50 μl of 1 μg/ml mouse anti-gpIII antibody was added to each well and reacted at 37° C. for one hour. After washing the wells three times with PBS containing 1% BSA, 50 μl of alkaline phosphatase-conjugated goat anti-mouse IgG antibody (TAGO INC. BURLINGAME Calif. 94010 USA) was added to each well, and further reacted at 37° C. for one hour. After washing the wells three times with PBS containing 1% BSA, 100 μl of 0.5M diethanolamine-HCl (pH 9.5) containing 1 mg/ml p-nitrophenylphosphate 2-sodium salt was added to each well and reacted at a room temperature for 40 minutes. The absorbance at 405 num corresponding to a yellow color was measured by a microplate reader (Molecular Devices USA), fraction containing the largest amount of gpIII was sterilized with ultraviolet radiation and used as an antigen for an in vitro stimulation. FIG. 1 shows the reactivity of each fraction to mouse anti-gpIII monoclonal antibody. In this case, fraction No. 10 was used as an antigen for the in vitro stimulation.

b) Immunization of lymphocytes with gpIII

Human spleen lymphocytes were suspended in RPMI 1640 medium (containing 2 mM glutamine, 1 mM sodium pyruvate, 0.02 mg/ml serine, 80 μg/ml gentamicin) supplemented with 10% FCS, and the suspension was gently overlaid on Ficoll (pharmacia LKB Biotechnology Inc. New Jersey 08855 USA), and centrifuged at 1500 rpm for 20 minutes, to separate lymphocytes present at the interface. The lymphocytes thus obtained were washed by centrifugation twice with RPMI 1640 containing 10% FCS, and adjusted to $3\times10^6$ cells/ml. Antigen for in vitro stimulation (VZV Oka) and PWM (pokeweed mitogen, GIBCO Laboratories Grand Island N.Y. 14072 USA) were added to 50 ng/ml and 20 μg/ml respectively, and incubation was carried out for 7 days.

c) Construction of hybridoma by cell fusion

First, $10^7$ of the human lymphocytes stimulated as described above in b) and $2\times10^7$ of mouse myeloma cells P3×63 Ag8U1 (P3U-1) were mixed, and the mixture was then washed by centrifugation once with RPMI 1640 medium and centrifuged at 1500 rpm for 5 minutes, to obtain a cell pellet. Then, 1 ml of 35% polyethylene glycol solution (5.75 ml of RPMI 1640+3.5 ml of polyethylene glycol #1000+0.75 ml of dimethylsulfoxide) was added thereon, and the cells were gently suspended. After one minute, 1 ml of RPMI 1640 was added, after 2 minutes 2 ml of RPMI 1640 was added, after a further 2 minutes 4 ml of HAT-GIT medium (GIT medium (Nippon Seiyaku, Tokyo) containing 95 μM hypoxanthine, 0.4 μM aminopterin, 1.6 μM thymidine, 5% fetal bovine serum, 80 μg/ml gentamicin) was added, and a further 2 minutes later, 8 ml of HAT-GIT medium was added, to finally prepare 50 ml of cell suspension with HAT-GIT medium. This suspension was distributed to a 96-well culture plate (Falcon 3075, Becton Dickinson and CO. OXNARD Calif. 93030 USA) in which $10^4$/well mouse peritoneal exudate cells had been inoculated, and incubation was carried out at 37° C. in 5% $CO_2$ while exchanging a half of the medium with a fresh HT-GIT (medium wherein aminopterin was omitted from the HAT-GIT), at an interval of one week. After about 3 weeks, several colonies of hybridoma cells per well were obtained.

d) Screening of anti-gpIII antibody: ELISA

Anti-gpIII antibodies produced in culture supernatants of hybridomas obtained as described above in c) were screened by ELISA using 2 antigen plates (monolayer plate and homogenate plate).

The monolayer plate was a 96-well plate on which VZV-infected cells were fixed with glutaraldehyde, and was prepared as follows.

Human embryonic lung cells (hereinafter abbreviated as HEL cells) cultured in Eagle's MEM (hereinafter abbreviated as MEM) containing 10% fetal calf serum (FCS) were dispersed with 0.25% trypsin solution, adjusted to $10^5$ cells/ml with MEM containing 10% FCS, and distributed to a 96-well culture plate at an amount of 0.1 ml/well. After culturing at 37° C. in 5% $CO_2$ for 2 days, a HEL cell monolayer was infected by adding $10^3$/well of VZV (Oka strain)-infected HEL cells. After a further culturing for 2 days, when a cytopathic effect (CPE) appeared in all cells, the cells were washed twice with PBS (+) (PBS containing 1 mM $CaCl_2$, 1 mM $MgCl_2$), and fixed with PBS (+) containing 0.1% glutaraldehyde at 37° C. for 10 minutes. After fixation, the cells were washed three times with PBS (−), 200 μl/well of PBS (+) containing 1% bovine serum albumin (BSA) was distributed, and the plate was allowed to stand for one hour and stored at 4° C. until use.

A homogenate plate was a 96-well plate on which a homogenate antigen prepared by sonication of VZV-infected cells had been coated, and prepared as follows.

To HEL cells cultured in a culture flask having a bottom area of 150 $cm^2$ (about $10^7$ cells/culture flask) were added $2\times10^6$ per flask of VZV (Oka strain)-infected cells, and incubation was carried out at 37° C. in 5% $CO_2$ for 2 days.

After 2 days, when CPE appeared in all cells, the infected cells were collected with PBS containing 1 mM ethylenediamine tetraacetic acid (EDTA), washed three times with PBS (+) by centrifugation at 1500 rpm for 5 minutes. Then $10^7$ infected cells were suspended in 1 ml of PBS (+) containing 1 mM PMSF (phenylmethylsulfonylfluoride), and sonicated at 50 W for one minute (Microson Ultrasonic cell disrupter MS-50 23 kHz HEAT SYSTEMS-ULTRASONICS INC. N.Y. USA).

The disrupted infected cell was centrifuged at 3000 rpm for 10 minutes, and the supernatant was used as a homogenate antigen. The antigen thus obtained was suspended in PBS (+) at a protein concentration of 4 µg/ml, and 50 µl/well of the suspension was distributed to a 96-well plate for ELISA (Falcon 3912) and reacted at 37° C. for one hour to coat the antigen on the plate. After washing each well with PBS (+) containing 1% BSA (washing buffer solution), PBS (+) containing 1% BSA was added thereon, and the plate was allowed to stand at 37° C. for one hour (blocking) and stored at 4° C. until use. Two kinds of plates thus prepared were used to carry out an ELISA as follows. First, 150 µl/well of culture supernatant of the hybridoma obtained as described above in c) was taken, and then 50 µl each of the supernatant was added to wells of the monolayer plate and the homogenate plate, and reacted at room temperature for one hour. After washing the wells three times with the washing buffer solution, 50 µl/well of a second antibody was added. As the second antibody, a horseradish peroxidase-conjugated goat anti-human IgG (TAGO INC. BURLINGAME Calif. 94010 USA) 1000-fold diluted with PBS containing 1% BSA for the monolayer plate, and alkaline phosphatase-conjugated goat anti-human IgG (TAGO) 2000-fold diluted with PBS containing 1% BSA for the homogenate plate were used. After reaction at room temperature for one hour, and washing the wells three times with the washing buffer solution, 100 µl/well of substrate solution was added. The substrate solution was a 0.1M citrate-phosphate buffer solution (pH 4.3) containing 5 mM hydrogen peroxide and 0.4 mg/ml TMBZ (tetramethylbenzidine hydrochloride: Dojin Kagaku Kenkyusho, Kumamoto, Japan) for the monolayer plate, or 0.5M diethanolamine-HCl buffer solution (pH 9.5) containing 0.6 mg/ml p-nitrophenylphosphate 2-sodium salt as a substrate and 0.25 mM magnesium chloride for the homogenate plate.

After the addition of the substrate, the absorbance was measured by a microplate reader (UV max Molecular Devices Palo-Alto Calif. 94304 USA). In the case of the monolayer plate, after 100 µl/well of 0.1N sulfuric acid was added to terminate coloring, the absorbance at a wavelength of 450 nm was measured, and in the case of the homogenate plate, the absorbance at a wavelength of 405 nm was measured.

Screening was carried out by selecting wells which were strongly colored on the monolayer plate but only weakly colored on the homogenate plate, in view of properties such that, although the anti-gpI antibody and anti-gpII antibody strongly react with both the monolayer plate and homogenate plate, the anti-gpIII antibody reacts only weakly with the monolayer plate.

Figure 2:
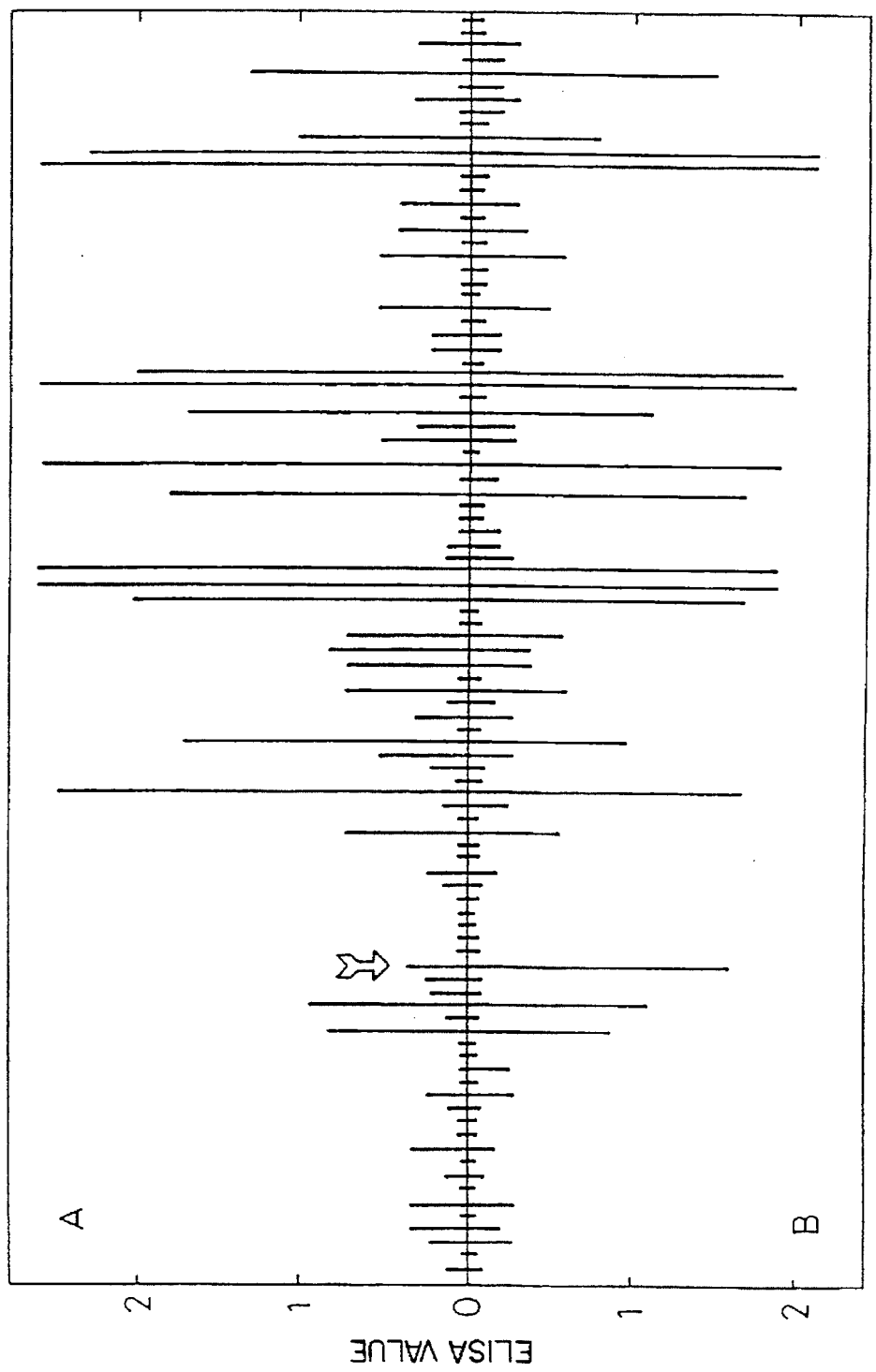
FIGS. 2(A and B) represent results of screening by ELISA using a cell homogenate plate and a cell monolayer plate, respectively. When each hybridoma supernatant in a 96-well culture plate was tested for reactivity in an ELISA, using a cell homogenate plate and cell monolayer plate, among 96 wells only one well strongly reacted with the cell monolayer plate but only weakly reacted with the cell homogenate plate. This is shown by an arrow. The hybridoma in this well produced an anti-gpIII HuMAb.

When hybridoma supernatants in the 96-well plate were screened, using a homogenate plate (A side of FIG. 2) and a monolayer plate (B side of FIG. 2), only one well (arrow) provided antibody to gpIII. This shows that it is difficult to select an anti-gpIII HuMAb by a screening using a conventional ELISA method.

Figure 3A:
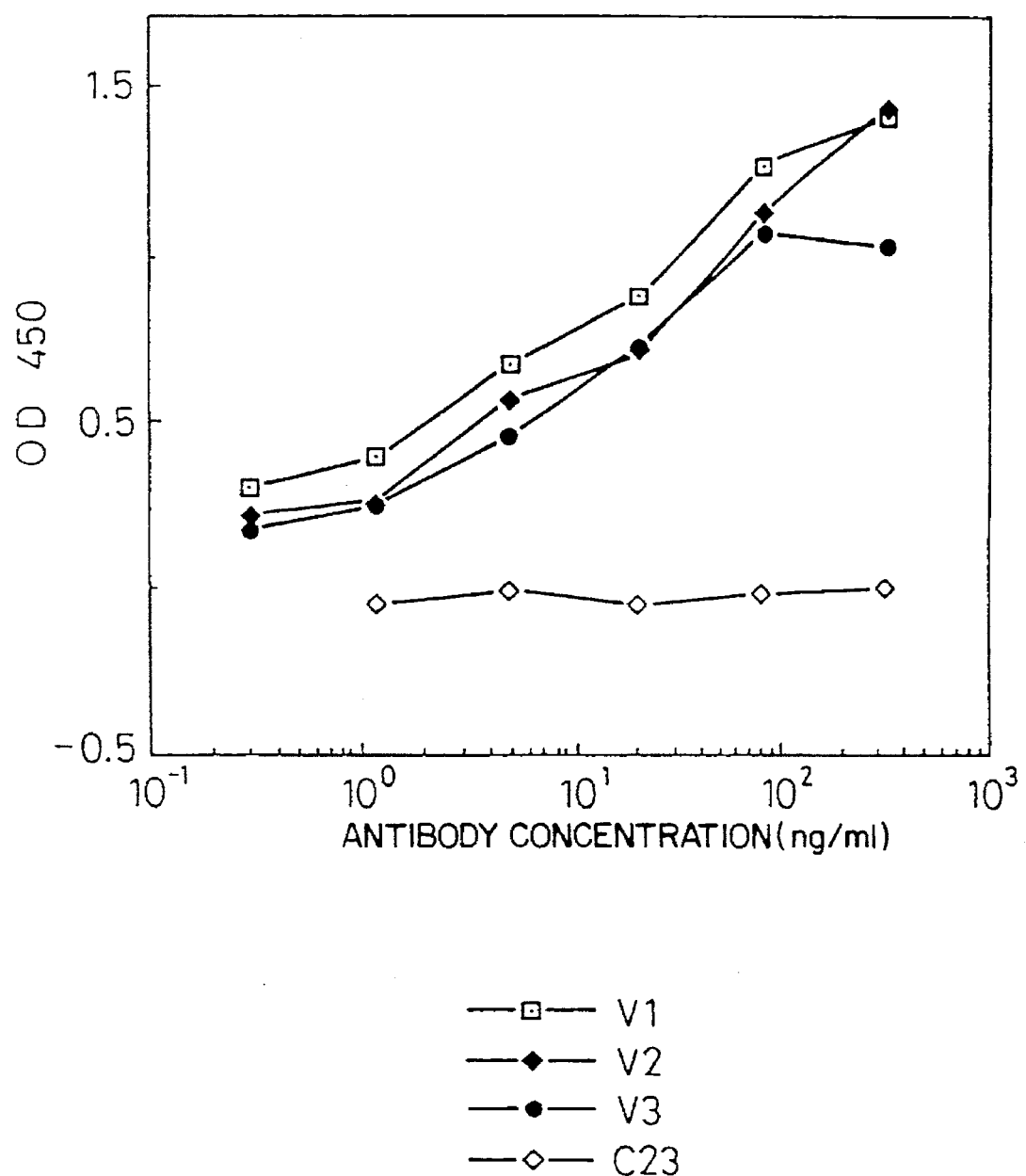
FIGS. 3A and 3B represent ELISA reactivities to a cell monolayer plate and a cell homogenate plate of anti-gpI HuMAb (V2), anti-gpII HuMAb (V1), and anti-gpIII HuMAb (V3), respectively. The anti-gpIII HuMAb strongly reacted with the cell monolayer plate, but only weakly reacted with the cell homogenate plate.
Figure 3B:
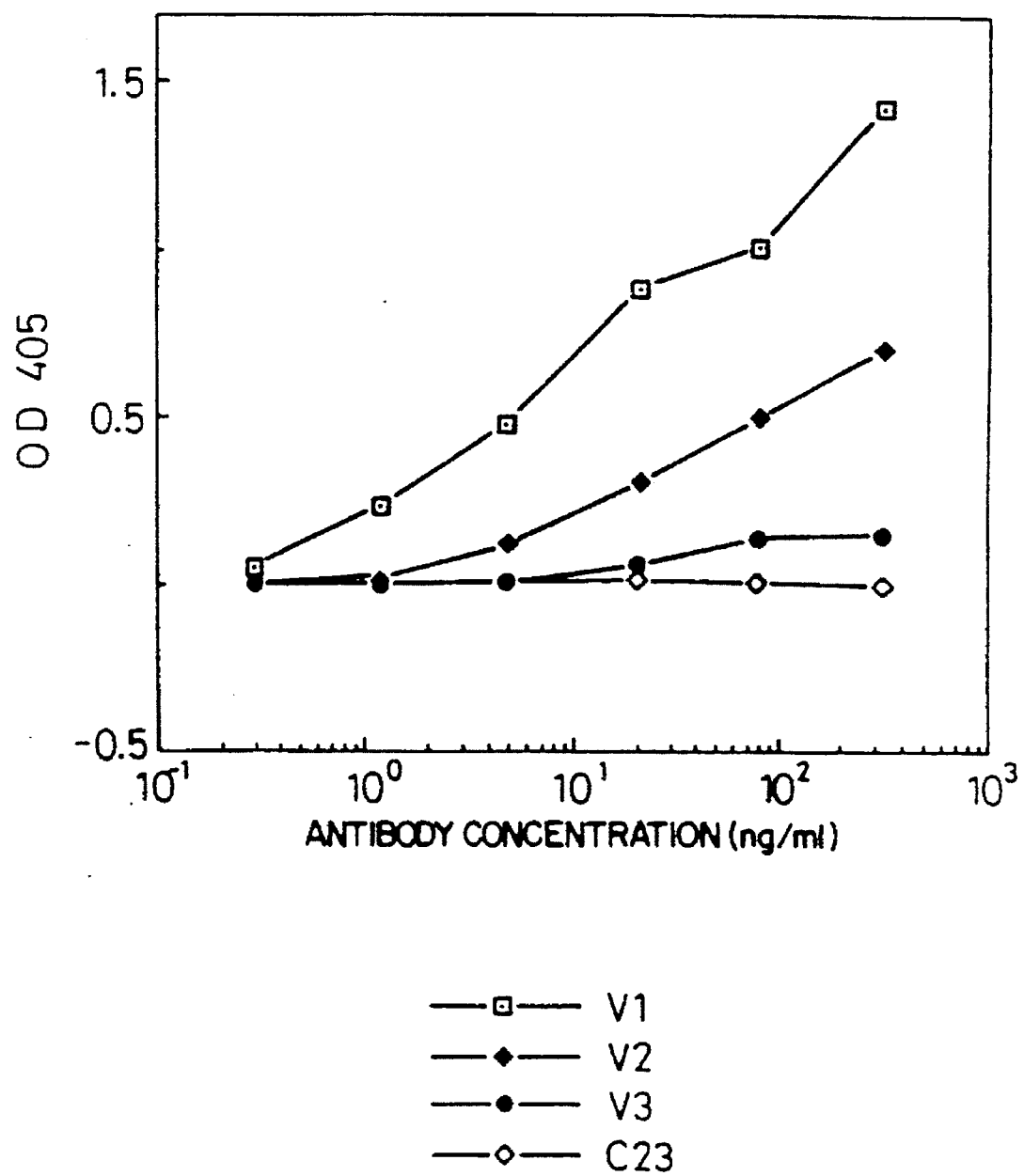

The reactivity of anti-gpI HuMAb (V2), anti-gpII HuMAb (V1) and anti-gpIII HuMAb (human MAb V3 obtained by the present invention) with a monolayer plate and a homogenate plate are shown in FIGS. 3A and 3B, respectively.

e) Screening by anti-viral activity: V-SIMA method (virus spread inhibition microassay)

Anti-gpIII HuMAb produced in hybridoma culture supernatants obtained in c) were screened by, in addition to the ELISA, the V-SIMA method. The HEL cell monolayer was cultured in a 96-well culture plate, to which were added 200/well of VZV (Oka strain)-infected cells (50 µl/well of 4000/ml infected cells), and immediately 150 µl/well of hybridoma culture supernatant obtained in c) were added. The cells were cultured at 37° C. in 5% $CO_2$ for 2 days, washed twice with PBS (+), and fixed with PBS (+) containing 0.1% glutaraldehyde at 37° C. for 10 minutes. After fixation, the wells were washed three times with PBS (+), 200 µl/well of PBS (+) containing 1% BSA was added, and the plate was allowed to stand at 37° C. for one hour for blocking. After sucking off the supernatant, 50 µl/well of 1 µg/ml V2 (anti-gpI HuMAb) was added and reacted at 37° C. for one hour. After the wells were washed three times with the washing buffer solution used in d), 50 µg/well of 200-fold diluted horseradish peroxidase-labeled goat anti-human IgG was added and reacted at 37° C. for one hour. After washing the wells three times with the washing buffer solution, 100 µl/well of a substrate solution comprising 0.05M Tris-HCl (pH 7.4) containing 5 mM hydrogen peroxide and 0.2 mg/ml of 4-chloro-1-naphthol (HRP color development reagent, Bio-Rad Laboratories Richmond Calif. 94804 USA) was added for color formation.

Figures 4A, 4B:
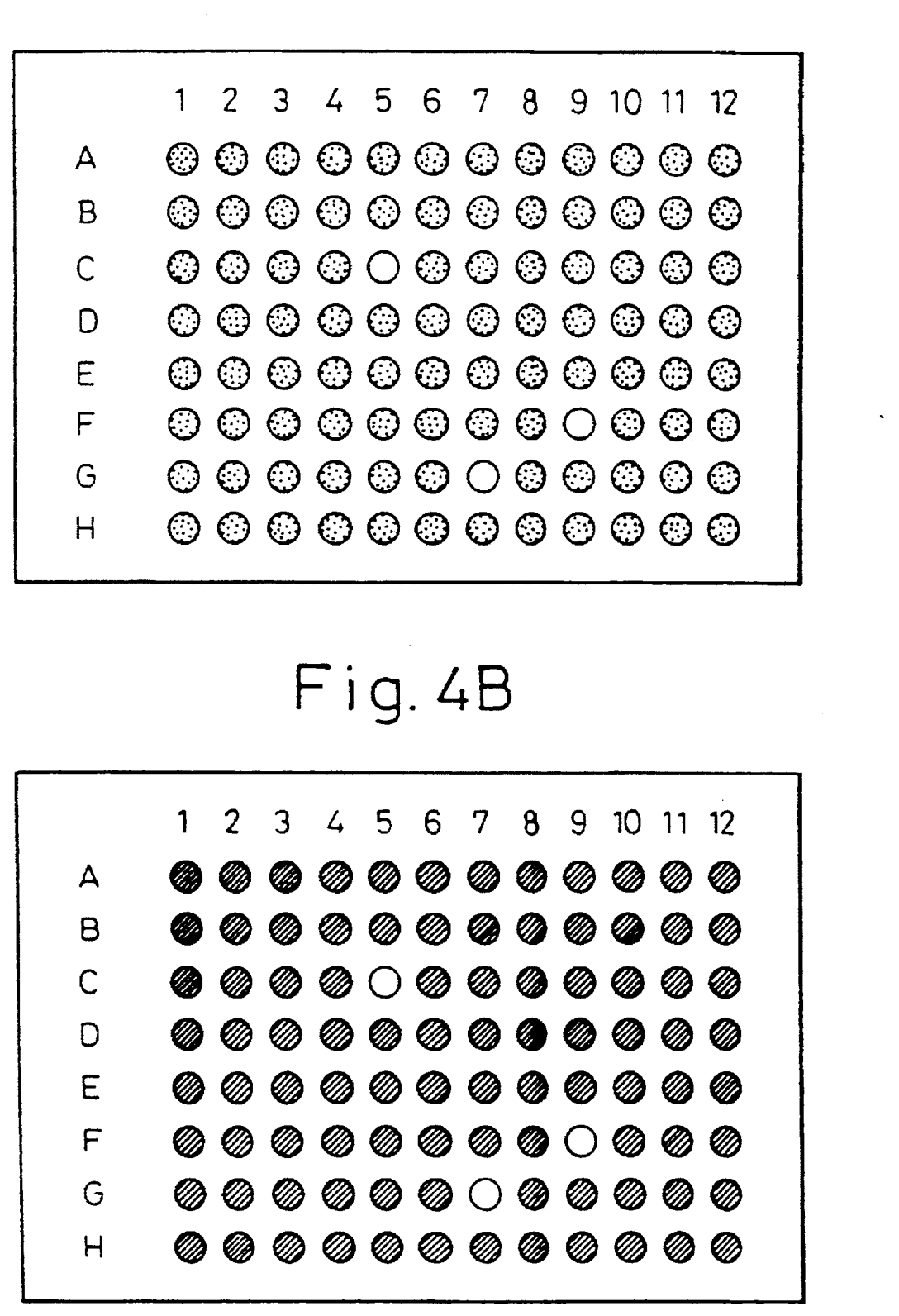

Hybridomas in wells exhibiting a vital spread inhibiting activity (weakly colored wells) were selected and cloned. A 96-well culture plate for V-SIMA used in the screening is shown in FIG. 4. Here, V-SIMA-positive hybridomas are C5, F9 and G7.

f) Cloning

Hybridomas obtained in d) and e) were cloned by a limiting dilution method, wherein $10^4$/well of peritoneal exudated cells of 8 to 10 weeks old ICR mouse were inoculated on a 96-well plate as feeder cells. Screened cells were diluted with GIT-HT containing 5% FCS and added such that each well contained 1 to 10 cells. Cloned hybridomas grown by culturing for 2 to 3 weeks were again screened by the method described above in d) and e), and similarly re-screened. In this manner, the hybridoma (V3) producing anti-gpIII HuMAb was established.

g) Culturing hybridoma and preparation of antibody

It was found that the hybridoma thus obtained can be cultured in RPMI 1640 medium containing 10% FCS, GIT medium, and serum-free medium ITES (one volume of RPMI 1640, one volume of DMEM, one volume of F12, 8.5 µg/ml insulin, 2 µg/ml transferrin, 20 µM ethanolamine, $2.5 \times 10^{-3}$M selenite), and stably produces an antibody for as long as at least 5 months.

The antibody contained in the culture supernatant obtained was able to be purified by adsorption on Protein A Sepharose 4B (Pharmacia Fine Chemicals AB Uppsala Sweden) and elution with a low pH buffer solution such as 0.1M acetate buffer solution (pH 3.0) containing 0.5M sodium chloride. For example, a supernatant obtained by culturing in GIT medium at a concentration of $5 \times 10^5$ cells/ml overnight contained 3 µg/ml antibody, and 5 l of the culture supernatant was purified with Protein A Sepharose 4B to obtain about 10 mg of HuMAb.

The H chain subclass of the HuMAb thus obtained was determined by SRID method (Serotec Ltd. Oxford OX 51 BR, England), and the L Chain type was determined by ELISA using an alkaline phosphatase-conjugated goat anti-human Lambda (TAGO) and an alkaline phosphatase-conjugated goat anti-Kappa antibody (TAGO). As a result, it was found that the V3 is IgG1, K (Kappa).

h) Identification of recognized antigen

A recognized antigen by the HuMAb obtained as described above in g) was identified by immunoprecipitation using SDS-PAGE (sodium dodecyl sulfate-polyacrylamide gel electrophoresis).

HEL monolayer cells ($5 \times 10^6$/ bottle) cultured in a culture bottle having a bottom area of 75 cm$^2$ were inoculated with ⅕ amount ($10^6$ cells/bottle) of VZV (Oka strain)-infected cells, and after 24 hours when at least 80% cytopathic effect (CPE) appeared, further incubation was carried out in a medium containing 18.5 MBq [$^{35}$S]-methionine (>48 TBq/ mmol Amersham International plc Buckinghamshire HP79LL England) for 18 hours to isotope-label the viral antigen. The culture medium used was ¹⁄₁₀ methionine MEM containing 2% dialyzed FCS.

Infected cells were washed twice with PBS, suspended in 2 mM EDTA-PBS, further washed once with PBS (+), and centrifuged at 1000 rpm for 5 minutes to form a pellet.

To this cell pellet was added 3 ml/$5 \times 10^6$ cells of RIPA buffer solution (20 mM Tris-HCl (pH 7.4) containing 1% Triton X-100, 1% sodium deoxycholate (DOC), 0.1% sodium dodecyl sulfate (SDS), 0.15M sodium chloride, 1 mM phenylmethylsulfonyl fluoride (PMSF) and 1 mM ethylenediaminetetraacetic acid (EDTA)), and the cells were solubilized by sonication. The sonicate was overlaid on RIPA buffer solution containing 60% sucrose, and ultracentrifuged at 100,000 Xg for one hour (Hitachi PRS50-2) to remove impurities, and the supernatant was used as an isotope-labeled antigen. This antigen ($10^7$ dpm/100 µl) and HuMAb (10 µg/100 µl) were mixed, and Protein A-Sepharose 4B, which had been swollen and blocked with non-labeled antigen of non-infected cells, was added in an amount of 3 mg beads powder, and a reaction was carried out at 4° C. for one hour.

The Protein A-Sepharose 4B on which an antigen-antibody complex had been adsorbed was washed, by centrifugation at 10,000 rpm for one minute, 5 times with RIPA buffer solution and twice with 10 mM Tris-HCl (pH 6.8), 100 µl of SDS-sample buffer (0.0625M Tris-HCl (pH 6.8) containing 10% glycerol, 5% β-mercaptoethanol, 2.3% SDS, 0.001% bromophenol blue), and the antigen-antibody complex was dissociated from Protein A-Sepharose by heating at 100° C. for 3 minutes. Protein A-Sepharose 4B was removed by centrifugation at 10,000 rpm for one minute to obtain a supernatant which was used as a sample for SDS PAGE.

An electrophoresis was carried out according to a standard Laemmli method (Laemmli U. K., Nature, Vol. 227, pp 680–685, 1970) using 10% polyacrylamide gel at 100 V for 5 hours.

After the end of the electrophoresis, the gel was fixed by soaking in a 50% methanol and 10% acetic acid solution for one hour, soaked in 1M sodium salicylic acid for 30 minutes, and dried by vacuum and heating on filter paper using a gel drier. The dried gel was then exposed to a KODAK X Ray-OMAT film at −70° C. for 1 to 2 days.

The result is shown in FIG. 5. The HuMAb (V3) precipitated a viral antigen of 118,000 Dalton. This antigen is gpIII. Note, HuMAb (V2) to gpI and HuMAb (V1) to gpII immunoprecipitated the molecular weights 90,000 and 55,000, and the molecular weights 108,000 and 62,000, respectively.

i) Neutralization of virus by anti-VZVgpIII.HuHAb

First, 20 µg/ml HuMAb purified with Protein A-Sepharose 4B was sequentially 3-fold diluted with MEM containing 10% FCS, and 200 µl of the diluted solution, 100 µl of $4 \times 10^3$ pfu/ml VZV solution, and 100 µl of 5-fold diluted guinia pig complement ($CH_{50}$=50 upon 5-fold dilution) or 100 µl of MEM containing 10% FCS were mixed, and reacted at 37° C. for one hour.

After the reaction, the virus HuMAb mixture (200 µl) was inoculated to HEL monolayer cells previously cultured in a 6-well culture plate (Falcon 3046) and adsorbed at 37° C. for one hour. After the adsorption, an MEM containing 0.5% agarose and 5% FCS was overlaid on the cells, which were then cultured at 37° C. in 5% $CO_3$ for 7 days. VZV-infected plaques were fixed with a 10% formaldehyde solution, stained with 0.15% methylene blue, and counted under an optical microscope. The antibody concentration which reduces the plaque number by 50% is shown as the $ED_{50}$.

As a result, the anti-gpIII HuMAb (V3) has a good neutralizing activity, as follows.

Having a neutralizing activity as high as 1700 to 14000 times that of normal human serum immunoglobulin (NH IgG).

Having a complement-independent neutralizing activity.

Having a high neutralizing activity compared with other anti VZV HuMAb, i.e., anti-gpI (V2) and anti-gpII (V1).

Having a high neutralizing activity against all of four VZV strains (3 laboratory-passaged strains and 1 clinical isolate).

The results are shown in Table 1.

TABLE 1

| Viral strains | $ED_{50}$ Value (µg/ml) | | | | | | | |
|---|---|---|---|---|---|---|---|---|
| | Without complement | | | | With Complement | | | |
| | Kawaguchi | Oka | CaQu | Kobayashi | Kawaguchi | Oka | CaQu | Kobayashi |
| V1 | 3.5 | 1.9 | 3.5 | 1.4 | 0.33 | 0.22 | 0.33 | 0.63 |
| V2 | >10 | >10 | >10 | >10 | 0.036 | 0.18 | 0.070 | 0.082 |
| V3 | 0.027 | 0.15 | 0.10 | 0.043 | 0.029 | 0.036 | 0.044 | 0.041 |
| NHIgG | 380 | 460 | 630 | 230 | 49 | 140 | 140 | 74 | j) Virus spread inhibiting activity (V-SIMA) of anti-VZV gpIII HuMAb

The virus spread inhibiting activity of anti-gpIII HuMAb purified as described above in g) was tested.

To a HEL cell monolayer previously cultured in a 96-well culture plate was added 100 pfu/well of VZV (Oka), and after infection at 37° C. for 2 hours, the wells were washed three times with PBS (+). Then 200 µl/well of HuMAb solution sequentially three-fold diluted with MEM containing 10% FCS was added, and incubation was carried out at 37° C. in 5% $CO_2$ for 7 days. When CPE in a well to which the antibody had not been added reached 100%, the wells were washed three times with PBS (+), and 200 µl/well of PBS (+) containing 0.1% glutaraldehyde was added for fixation.

Figure 6:
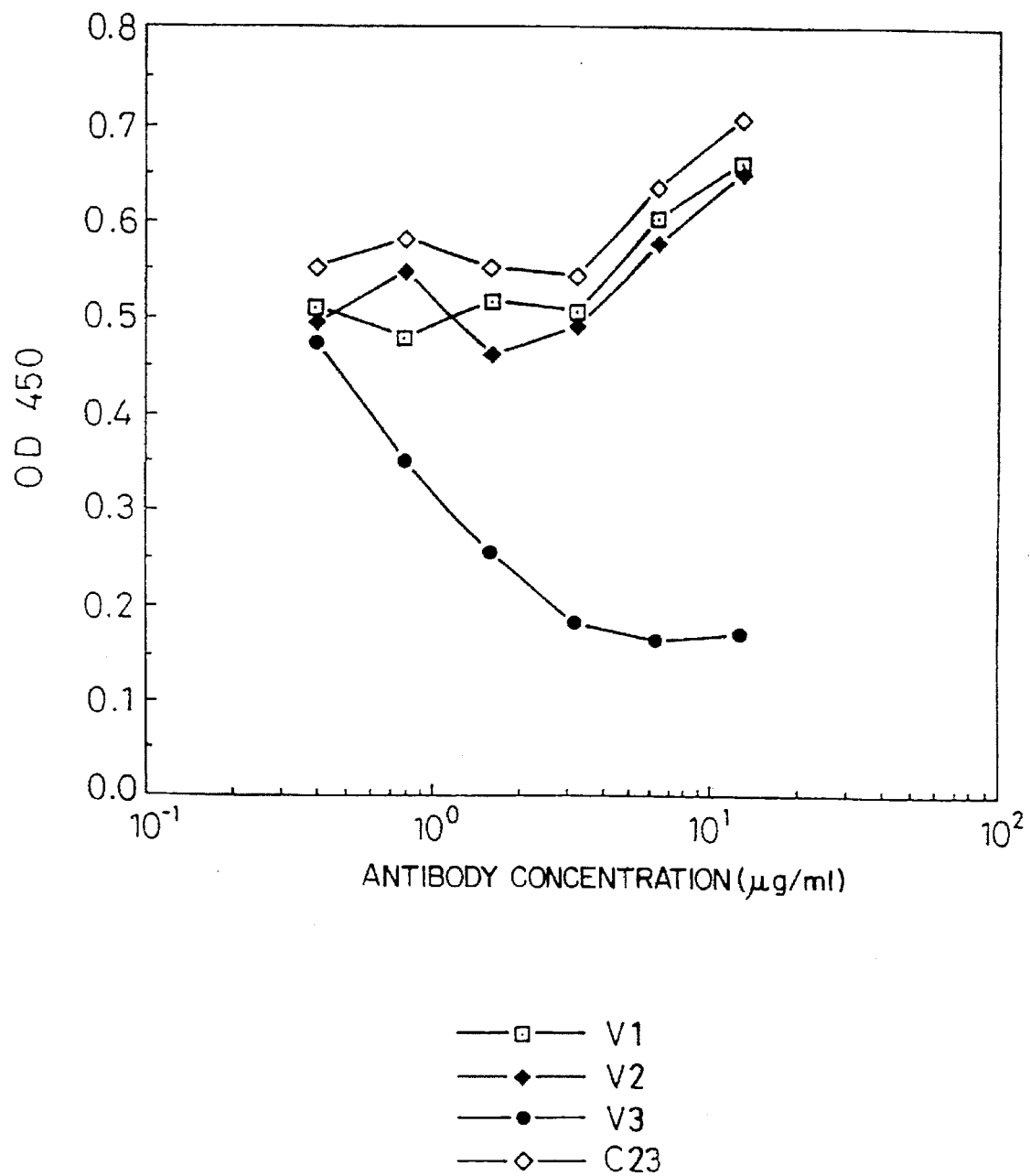
FIG. 6 shows virus spread-inhibiting activity of various MAbs. Anti-gpIII HuMAb (V3) exhibits a 50% virus spread-inhibiting activity at a concentration of 1 µg/ml.

Next, spread of infection of VZV was measured by a method similar to an ELISA, using a monolayer plate as described in d). The result is shown in FIG. 6. Where the VZV infection is inhibited the absorbance from the ELISA is low, and where the VZV infection is not inhibited, it is high. The anti-gpIII HuMAb (V3) inhibited spread of VZV infection, and its $ED_{50}$ value ($ED_{50}$ value is an HuMAb concentration which provides a 50% absorbance, where an absorbance in the case when an expansion of VZV infection is not inhibited is defined as 0% and an absorbance in the case when an expansion of VZV infection is completely inhibited is defined as 100%) was 1 µg/ml. Other anti-VZV HuMAb anti-gpI (V2) and anti-gpII (V1), and anti-HCMV HuMAb (C23) did not inhibit spread of VZV infection at all at a concentration of 10 µg/ml.

k) Antibody dependent cell mediated cytotoxicity (ADCC) of anti-VZV gpIII HuMAb

To HEL monolayer cells ($5 \times 10^6$ cells/bottle) cultured in a culture bottle having a bottom area of 75 cm², VZV (Oka)-infected cells were inoculated. After 24 hours, when at least an 80% cytopathic effect appeared, the infected cells were floated by PBS (−) containing 0.02% EDTA and 0.1% trypsin. The cells were resuspended in RPMI 1640 containing 20% FCS to obtain $1 \times 10^6$ cells/ml cell suspension, and 7.4M Bq [$^{51}$Cr] sodium chromate (Na[$^{51}$Cr]O$_4$; 9.3–19 GBq/mg Cr; Amersham International pIc., Buckinghamshire HP79LL England) was added thereon and reacted at 37° C. for one hour to label isotopically. The isotopically labeled infected cells were washed 5 times with an RPMI 1640 medium containing 20% FCS, and resuspended to obtain $5 \times 10^4$ cells/ml cell suspension for use as target cells.

As effector cells, human spleen lymphocytes were used. Namely, human spleen lymphocytes were gently overlaid on Ficall, and centrifuged at 1500 rpm for 20 minutes to precipitate lymphocytes at the interface. The obtained lymphocytes were washed twice with RPMI 1640 containing 20% FCS, and adjusted to $1 \times 10^7$ cells/ml.

To a 96-well round bottom culture plate were added 100 µl of target cells, 50 µl of a stepwise-diluted antibody solution, and 100 µl of effector cells, and were reacted at 37° C. for 18 hours.

For a total $^{51}$Cr release, 2% Triton X-100 was added in place of the antibody solution, and for a spontaneous $^{51}$Cr release, the RPMI 1640 medium containing 20% FCS was added in place of the antibody solution.

After finishing the reaction, the supernatant was recovered with a Skatron supernatant collection system (Skatron, Norway), and the $^{15}$Cr value (dpm) released into the supernatant was measured using a gamma scintillation counter (Aloka, Japan). ADCC activity of each antibody is expressed by % cytotoxicity against VZV-infected cells according to the following equation:

$$\frac{^{51}\text{Cr release (dpm)} - \text{Spontaneous } ^{51}\text{Cr}}{\text{of each antibody} \quad \text{release (dpm)}} \times 100 \, (\%)$$
$$\frac{}{\text{Total } ^{51}\text{Cr} - \text{Spontaneous } ^{51}\text{Cr}}$$
$$\text{release (dpm)} \quad \text{release (dpm)}$$

Figure 7:
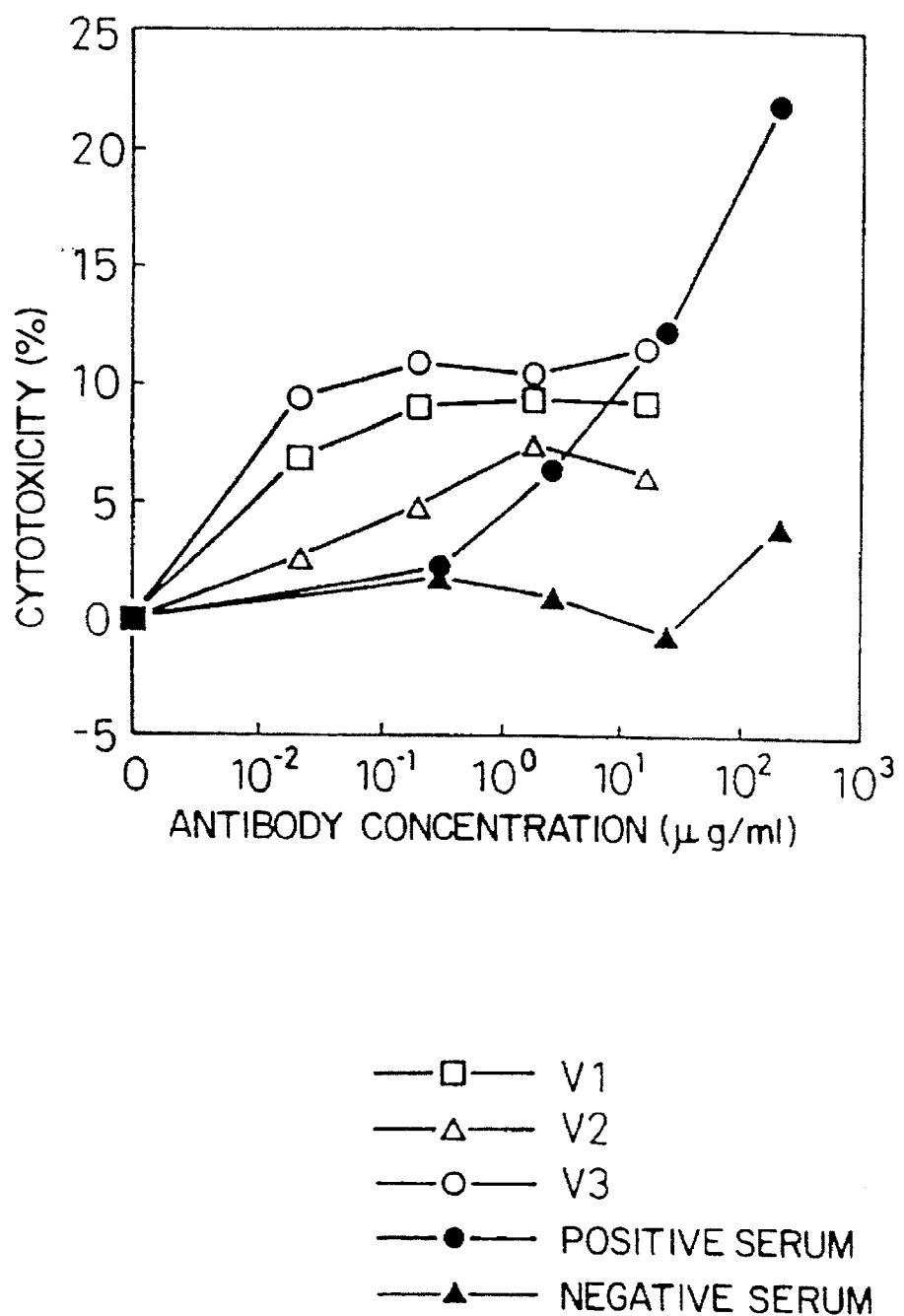
FIG. 7 shows ADCC activity of anti-gpIII HuMAb (V3). The V3 exhibited about a 10% cytotoxicity at 20 ng/ml.

As a result V3 (anti-gpIII HuMAb) exhibited ADCC activity at a concentration as low as 20 ng/ml. The result is shown in FIG. 7.

Reference to deposited microorganism and depository authority under Rule 13-2:

Depository authority: Fermentation Research Institute, Agency of Industrial Science and Technology Address: 1-3 Higashi 1-chome, Tukuba-shi, Ibaraki-ken, Japan Deposition Number and date:

Cell line V3β1F4 (subclone of hybridoma V3 producing anti-VZV gpIII HuMAb)

Deposition date: Feb. 21, 1990

Deposition No.: FERM BP-2765

INDUSTRIAL APPLICABILITY

The present MAb to VZV is considered useful for a diagnosis, prophylaxis and treatment of VZV-infectious diseases.

What is claimed is:

1. A human monoclonal antibody specific for glycoprotein gpIII of varicella zoster virus (VZV) having the following properties:

(1) inhibits cell-to-cell infection of VZV at a concentration of 10 µg/ml; and (2) has VZV neutralizing activity as high as 1700 to 14000 times that of normal human serum immunoglobulin.

2. The human monoclonal antibody according to claim 1, having antibody dependent cell mediated cytotoxicity activity against VZV-infected cells.

3. A hybridoma that produces the human monoclonal antibody of claim 2 or 1, or cell line derived therefrom.

4. A cell line deposited with Fermentation Research Institute Agency of Industrial Science and Technology having deposition number FERM BP-2765, or a cell line derived therefrom.

* * * * *